(12) United States Patent
Randle et al.

(10) Patent No.: US 9,078,676 B2
(45) Date of Patent: Jul. 14, 2015

(54) PATELLA DRILLING SYSTEM

(75) Inventors: Raymond E. Randle, Mudaeeraba (AU);
Martin W. Roche, Ft. Lauderdale, FL (US); Abraham P. Wright, Winona Lake, IN (US)

(73) Assignee: DEPUY (IRELAND), Cork (IE)

( * ) Notice: Subject to any disclaimer, the term of this patent is extended or adjusted under 35 U.S.C. 154(b) by 391 days.

(21) Appl. No.: 13/548,661

(22) Filed: Jul. 13, 2012

(65) Prior Publication Data

US 2013/0079789 A1 Mar. 28, 2013

Related U.S. Application Data

(60) Provisional application No. 61/540,053, filed on Sep. 28, 2011.

(51) Int. Cl.
*A61B 17/17* (2006.01)
*A61F 2/38* (2006.01)
*A61F 2/30* (2006.01)

(52) U.S. Cl.
CPC ........... *A61B 17/1767* (2013.01); *A61F 2/3877* (2013.01); *A61F 2002/30225* (2013.01)

(58) Field of Classification Search
CPC ............. A61B 17/1677; A61B 17/158; A61B 17/1767; A61B 17/8866; A61B 17/1764; A61B 2019/304
USPC .................... 606/79, 80, 86 R, 87–88, 96–98
See application file for complete search history.

(56) References Cited

U.S. PATENT DOCUMENTS

| | | | |
|---|---|---|---|
| 2,181,746 A | 11/1939 | Siebrandt | |
| 3,835,849 A | 9/1974 | McGuire | |
| 4,009,712 A * | 3/1977 | Burstein et al. | 606/67 |
| D260,927 S | 9/1981 | Glenn | |
| D281,622 S | 12/1985 | Diamond | |
| 4,565,192 A | 1/1986 | Shapiro | |
| 4,633,862 A | 1/1987 | Petersen | |
| 5,002,547 A | 3/1991 | Poggie et al. | |

(Continued)

FOREIGN PATENT DOCUMENTS

| | | |
|---|---|---|
| EP | 791335 A1 | 8/1997 |
| EP | 992222 A2 | 4/2000 |

(Continued)

OTHER PUBLICATIONS

Australian Search Report for Patent Application No. 2012227341 Dated Jun. 13, 2014, 3 Pages.

(Continued)

*Primary Examiner* — David Bates
*Assistant Examiner* — Samuel Hanna (57) ABSTRACT

A patella drilling system includes a clamp and a patella drill guide. The clamp includes an arm with a pointed tip that is received in a dimple on the surface of the patella drill guide and another arm with a bone-gripping member spaced from the tip. The clamp is used to hold the patella drill guide firmly against the resected posterior surface of the patella while the surgeon drills into the patella to form holes for mounting pegs on the implant. The clamp may allow the patella drill guide to be pivoted while clamped so that the orientations of the guide bores may be optimized. The system includes an optional cap that may be used on the pointed tip of the clamp to hold the implant firmly in place while the bone cement sets.

13 Claims, 4 Drawing Sheets

(56) References Cited

U.S. PATENT DOCUMENTS

| | | | |
|---|---|---|---|
| 5,021,055 A | 6/1991 | Burkinshaw | |
| 5,108,401 A | 4/1992 | Insall et al. | |
| 5,116,338 A | 5/1992 | Poggie | |
| 5,129,907 A | 7/1992 | Heldreth | |
| 5,129,908 A | 7/1992 | Petersen | |
| 5,147,365 A | 9/1992 | Whitlock et al. | |
| 5,222,955 A | 6/1993 | Mikhail | |
| 5,250,050 A | 10/1993 | Poggie et al. | |
| 5,284,482 A | 2/1994 | Mikhail | |
| 5,284,485 A | 2/1994 | Kammerer et al. | |
| 5,312,409 A | 5/1994 | McLaughlin | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price et al. | |
| 5,520,692 A | 5/1996 | Ferrante | |
| 5,536,271 A | 7/1996 | Daly | |
| 5,542,947 A | 8/1996 | Treacy | |
| D373,635 S | 9/1996 | Price et al. | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,716,362 A | 2/1998 | Treacy | |
| 5,827,279 A | 10/1998 | Hughett et al. | |
| 5,916,217 A | 6/1999 | Manthrop et al. | |
| 5,941,884 A | 8/1999 | Corvelli et al. | |
| 5,944,723 A | 8/1999 | Colleran | |
| 5,968,051 A | 10/1999 | Luckman et al. | |
| 6,010,509 A * | 1/2000 | Delgado et al. | 606/88 |
| 6,056,754 A | 5/2000 | Haines et al. | |
| 6,074,425 A | 6/2000 | Pappas | |
| 6,190,391 B1 | 2/2001 | Stubbs | |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,855,150 B1 | 2/2005 | Linehan | |
| 6,866,667 B2 | 3/2005 | Wood et al. | |
| 6,923,812 B1 | 8/2005 | Wellisz | |
| D549,331 S | 8/2007 | Tomatsu et al. | |
| 7,344,540 B2 | 3/2008 | Smucker et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn | |
| D667,552 S | 9/2012 | Claypool | |
| D667,953 S | 9/2012 | Wright | |
| 2002/0115987 A1 | 8/2002 | Hildwein et al. | |
| 2003/0163137 A1 | 8/2003 | Smucker et al. | |
| 2004/0153066 A1 | 8/2004 | Coon | |
| 2004/0162561 A1 | 8/2004 | Marchyn | |
| 2005/0240196 A1 | 10/2005 | Davis et al. | |
| 2006/0142777 A1 | 6/2006 | Bastian | |
| 2007/0118141 A1 | 5/2007 | Marchyn et al. | |
| 2007/0233142 A1 | 10/2007 | Oliver | |
| 2007/0260227 A1 | 11/2007 | Phan | |
| 2007/0270850 A1 * | 11/2007 | Geissler | 606/69 |
| 2008/0097450 A1 | 4/2008 | Brown et al. | |
| 2008/0114366 A1 | 5/2008 | Smucker et al. | |
| 2008/0177394 A1 | 7/2008 | Chauhan | |
| 2008/0228190 A1 | 9/2008 | Sherry et al. | |
| 2008/0306484 A1 | 12/2008 | Coon | |
| 2009/0264737 A1 | 10/2009 | Haechler et al. | |
| 2009/0326661 A1 | 12/2009 | Wright et al. | |
| 2010/0004691 A1 * | 1/2010 | Amato et al. | 606/280 |
| 2010/0030223 A1 | 2/2010 | Kellar | |
| 2010/0152742 A1 | 6/2010 | Nevelös et al. | |
| 2010/0168753 A1 | 7/2010 | Edwards et al. | |
| 2011/0066193 A1 | 3/2011 | Lang | |
| 2012/0078261 A1 | 3/2012 | Kecman et al. | |
| 2013/0023883 A1 | 1/2013 | Wright | |
| 2013/0023890 A1 | 1/2013 | Kecman | |
| 2013/0030443 A1 | 1/2013 | Wright | |
| 2013/0030539 A1 | 1/2013 | Wright | |
| 2013/0035693 A1 | 2/2013 | Wright | |
| 2013/0079787 A1 | 3/2013 | Jones | |
| 2013/0079789 A1 | 3/2013 | Randle | |
| 2013/0211410 A1 | 8/2013 | Landes | |

FOREIGN PATENT DOCUMENTS

| | | |
|---|---|---|
| EP | 1723916 A1 | 11/2006 |
| EP | 1967143 A2 | 9/2008 |
| EP | 2574314 A1 | 4/2013 |
| FR | 2737848 A1 | 2/1997 |
| WO | WO 9945856 A1 | 9/1999 |
| WO | WO 2005110249 A1 | 11/2005 |
| WO | WO 2008112996 A1 | 9/2008 |

OTHER PUBLICATIONS

Depuy International Ltd., PFC Sigma Rotating Platform Knee System with MBT Tray, Surgical Technique Brochure, 2003, (43 pages), Cat. No. 9068-96-000, DePuy International Ltd., Leeds, England.

Depuy Orthopaedics, Inc., LCS High Performance Instruments, Surgical Technique Guide, 2008, (44 pages), Pub. No. 0612-85-506, DePuy Orthopaedics, Inc., Warsaw, IN.

Depuy Orthopaedics, Inc., Sigma High Performance Instruments, Classic Surgical Technique, 2010, (52 pages), Pub. No. 0612-89-510, DePuy Orthopaedics, Inc., Warsaw, IN.

Depuy Orthopaedics, Inc., Sigma High Performance Instruments, Design Rationale, 2009, (12 pages), Pub. No. 0612-54-506 (Rev.2), DePuy Orthopaedics, Inc., Warsaw, IN.

European Search Report, European Patent Application No. 11175824.9-2310, Dec. 16, 2011, (8 pages).

European Search Report, European Patent Application No. 11175824.9-2310, Mar. 1, 2013 (7 pages).

European Search Report, European Patent Application No. 12186675.0-2310, Dated Dec. 12, 2012 (7 Pages).

European Search Report, European Patent Application No. 12186728.7-2310, Dated Dec. 14, 2012 (8 Pages).

European Search Report, European Patent Application No. 12186700.6-2310, Dec. 13, 2012 (8 Pages).

\* cited by examiner

PATELLA DRILLING SYSTEM

CROSS-REFERENCE TO RELATED APPLICATION

This application claims priority to U.S. Prov. App. No. 61/540,053 filed Sep. 28, 2011, entitled "Patella Drilling System," which is incorporated by reference herein in its entirety.

TECHNICAL FIELD

The present disclosure relates generally to orthopaedic surgical instruments and more particularly to patella drilling instruments.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, an orthopaedic prosthesis is implanted into the patient's patella. Specifically, a prosthetic patella implant component is secured to the patient's natural patella such that its posterior surface articulates with a femoral component during extension and flexion of the knee.

Conventional prosthetic patellas may have a dome-shaped polymer bearing or an anatomic or conforming polymer bearing. Anatomic or conforming bearings are designed to conform with the bearing surfaces of the femur. Dome patella components allow for greater movement between the patella component and the femoral component of the knee prosthesis, whereas anatomic patella components are more constrained relative to the femoral component. An example of dome-shaped prosthetic patella is disclosed in U.S. Pat. No. 5,593,450. An example of such an anatomic prosthetic patella is disclosed in U.S. Pat. No. 6,074,425.

To facilitate the replacement of the articulating surface of the natural patella with the prosthetic patella, orthopaedic surgeons use a variety of orthopaedic surgical instruments such as, for example, saws, drills, mills or reamers to resect the posterior surface of the patella and then to prepare the resected surface for fixation of the prosthetic patella.

Common fixation elements for prosthetic patellae include one or more pegs extending out from the bone-facing (anterior) surface to be received in complementary recesses or holes drilled or reamed into the patella. To prepare the patella to receive such a prosthetic patella, the surgeon may resect the posterior portion of the patella to define a flat surface and then uses a drill guide and drill to drill the hole or holes into the resected surface of the patella. However, it is difficult to hold the patella drill guide stationary against the patella while drilling, particularly when the patella is everted: this surgical step may require one hand to hold the patella, another hand to hold the drill guide and a third hand to drill the holes. Also, when cementing the patella implant to the prepared patellar surface, it may be difficult for the surgeon to hold the patella and patella implant in place.

SUMMARY

The present invention provides a patella drilling system that allows the surgeon to hold the patella and the patella drill guide together with a single hand while drilling with the other hand. Optionally, the patella drilling system contains an additional component that allows the surgeon to clamp the patella implant component to the prepared patella surface to allow the cement to set.

In an illustrative embodiment, the present invention provides a patella drilling system that includes a patella drill guide and a clamp. The patella drill guide has a flat patella bone-facing surface and an opposite upper surface. A drill guide bore extends from the upper surface to and through the flat patella bone-facing surface. The drill guide bore has a central longitudinal axis that is perpendicular to the flat patelle bone-facing surface. The upper surface of the patella drill guide has a recess separate from the drill guide bore.

The recess may comprise an indentation or dimple in the upper surface of the patella drill guide, or could comprise a bore.

The clamp has two arms, and each arm has two ends. The first end of the first arm has a free end segment adjacent to a contiguous segment. The free end segment has a tip that is sized and shaped to be received in the recess in the upper surface of the patella drill guide. The first end of the second arm has a bone-gripping member.

The first and second arms are movable with respect to each other to a position wherein the tip of the first arm is received within the recess of the patella drill guide and the bone-gripping member extends toward the bone-facing surface of the patella drill guide. Thus, the patella drill guide can be clamped to the patella during surgery to facilitate preparation of the patella to receive the implant.

In a more particular embodiment, the bone-gripping member and the second arm comprise discrete components connected through a pivotal connection.

In another more particular embodiment, the first arm and second arm are connected through a pivotal connection and are pivotable with respect to each other to a position wherein the end segment of the first arm is oriented substantially perpendicular to the patella bone-facing surface of the drill guide. In this embodiment, the free end segment and the contiguous segment may be shaped to define an acute angle between them.

In another more particular embodiment, when the patella drill guide is mounted on a patella, with the bone-gripping member engaging one surface of the patella, with the patella bone-facing surface engaging another surface of the patella and with the tip received in the recess, the patella drill guide is pivotable with respect to the clamp about an axis of rotation through the tip and through the bone-gripping member, the axis being substantially perpendicular to the patella bone-facing surface.

In another more particular embodiment, the bone-gripping member comprises a base and a plurality of spikes extending out from the base. In this embodiment, the base of the bone-gripping member may be connected to the first end of the second arm through a pivotal connection.

In another more particular embodiment, the recess and the drill guide bore have different diameters. In any of the embodiments, the recess and the drill guide bore may have different depths.

In another more particular embodiment, the recess extends from the upper surface of the drill guide bore but does not extend through the patella bone-facing surface of the patella drill guide.

In another more particular embodiment, the patella drilling system also includes a cap. The cap comprises a body having an end surface and an aperture overlying the end surface, wherein the aperture is sized and shaped to be complementary to at least a portion of the free end segment of the first arm so that the cap may be selectively mounted on the free end segment of the first arm. In this embodiment, the end surface of the cap may have a surface area greater than the surface area of the tip of the first arm of the clamp.

In another particular embodiment, the patella drill guide has an edge extending between the flat patella bone-facing surface and the opposite upper surface and this edge includes a plurality of spaced openings. In this embodiment, the upper surface of the drill guide may include indicia (and, more particularly, sizing indicia) adjacent to the spaced openings. These spaced openings may be sized and shaped so that portions of the resected surface of the patella are visible through the spaced openings. In a particular embodiment, the portion of the patella drill guide adjacent to the drill guide bore is thicker than the portions adjacent to the spaced openings.

In any of the above embodiments, the patella drill guide may have a plurality of spaced drill guide bores extending from the upper surface to and through the flat patella bone-facing surface. In such embodiments, the recess is spaced from the spaced drill guide bores and may be equidistant from each drill guide bore. For embodiments wherein the patella drill guide includes an edge with spaced openings, the recess and spaced drill guide bores may be spaced from the spaced openings.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior and posterior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
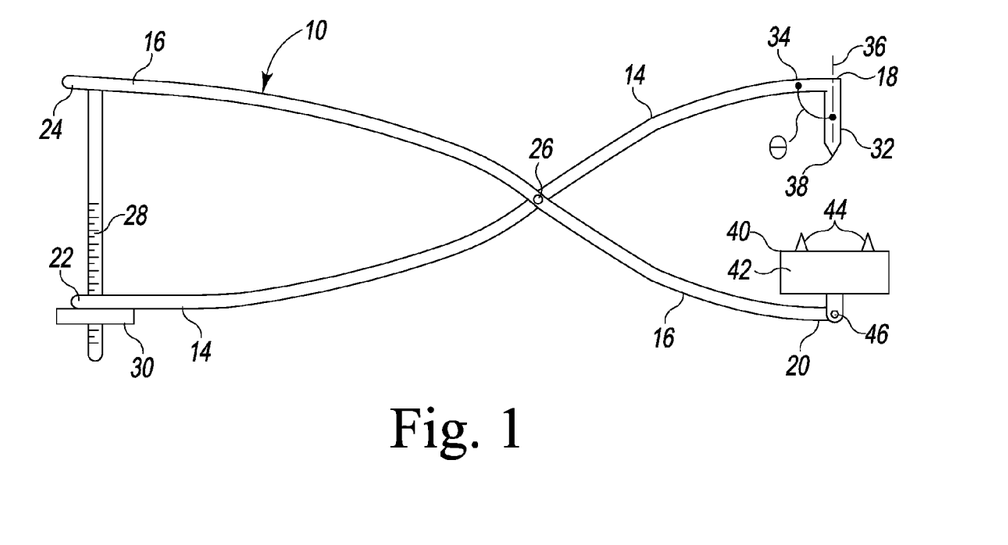
FIG. 1 is a side elevation of an illustrative clamp that may be used in the patella drilling system of the present invention.
Figure 2:
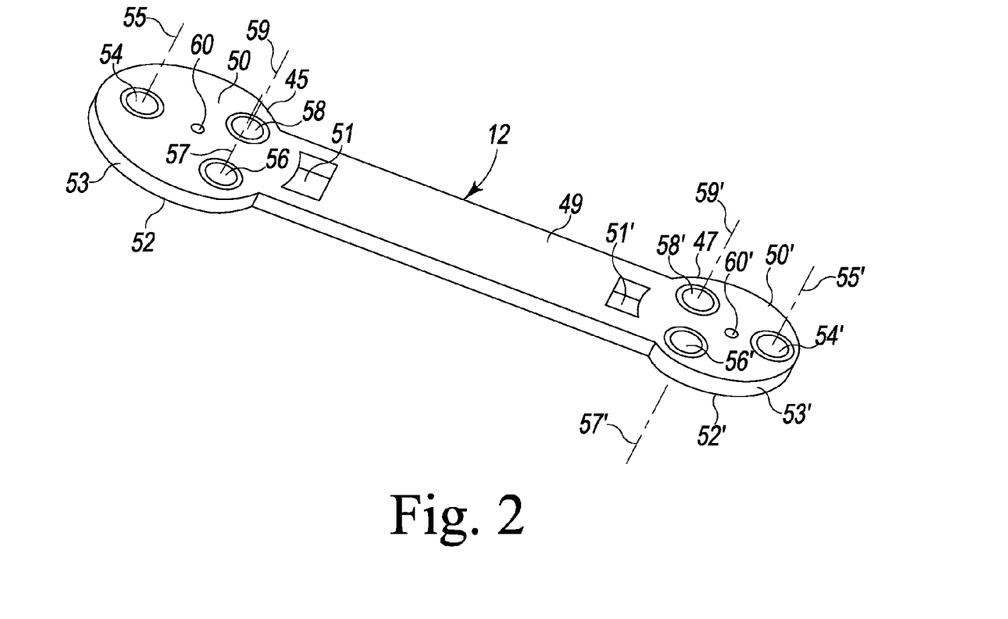
FIG. 2 is a perspective view of an illustrative patella drill guide that may be used in the patella drilling system of the present invention.

Referring to FIG. 1, an illustrative embodiment of a clamp 10 is illustrated. FIG. 2 illustrates an example of a patella drill guide 12. Together, the clamp 10 and the patella drill guide 12 define a patella drilling system incorporating the principles of the present invention.

The illustrated clamp 10 comprises a first arm 14 and a second arm 16. Each arm 14, 16 has two ends: first ends 18, 20 and second ends 22, 24. The arms 14, 16 are connected to each other through a pivotal connection 26. The pivotal connection 26 is located between the first ends 18, 20 and the second ends 22, 24 of the arms 14, 16, and may comprise a pin received in bores or the like, for example.

In the illustrated embodiment, the arms 14, 16 of the clamp 10 are shaped so that the first end 18 of the first arm 14 may be spaced from the first end 20 of the second arm 16 and the second end 22 of the first arm 14 may be spaced from the second end 24 of the second arm 16. Because of the shape of the arms 14, 16 and the pivotal connection 26, decreasing the spacing between the second ends 22, 24 also decreases the spacing between the first ends 18, 20 of the arms 14, 16. The illustrated clamp 10 includes a locking mechanism to lock the distance between the second ends 22, 24 of the arms 14, 16.

The illustrated locking mechanism comprises a threaded rod 28 having one end fixed to one arm 16 and extending through an aperture (not shown) in the other arm 14; a wing nut 30 is mounted on the portion of the rod extending through the aperture. With such a locking mechanism, the surgeon can lock the maximum separation between the second ends 22, 24 of the arms 14, 16, thereby locking the maximum separation between the first ends 18, 20 and can intraoperatively tighten the clamp by turning the wing nut 30. The illustrated threaded rod 28 and wing nut 30 are one example of a locking mechanism that could be employed; it will be appreciated that any standard locking mechanism or biasing mechanism can be employed if the mechanism allows for maintaining the clamping force between the first ends 18, 20 without continued pressure exerted by the surgeon. For example, a ratchet and pawl could be used as a locking mechanism.

The first end 18 of the first arm 14 of the clamp 10 includes a free end segment 32 and an contiguous segment 34 adjacent to the free end segment 32. As illustrated in FIG. 1, the free end segment 32 has a central longitudinal axis 36. An acute angle θ is defined between the axis 36 and the contiguous segment 34; this angle is shown in FIG. 1. Acute angle θ is about 85° in the illustrated embodiment, although it should be understood that the present invention is not limited to any particular angle unless expressly called for in the claims.

The first end 18 of the first arm 14 of the clamp 10 also includes a tip 38 at the end of the free end segment 32. The tip 38 in the illustrated embodiment generally comprises a pointed portion having a conical shape, although it should be appreciated that other shapes may be used.

The first end 18 of the second arm 16 of the clamp includes a bone-gripping member 40. The illustrated bone gripping member 40 comprises a base 42 and a plurality of spikes 44 extending from the base 42 toward the tip 38 of the first arm 14. In the illustrated embodiment, the bone gripping member 40 is a discrete component connected to the first end 18 of the second arm 16 through a pivotal connection 46 at the base 42. This pivotal connection may comprise a pin received in a bore or the like, for example. This pivotal connection 46 allows for adjustment of the orientation of the bone-gripping member 40 intraoperatively so that all the spikes 44 may grip the anterior surface of the patella.

Turning now to the patella drill guide 12, FIGS. 2-5 illustrate that the patella drill guide comprises a first end portion 45 and a second end portion 47 connected by an arm 49. At the intersections of the arm 49 and the two end portions 45, 47, the first illustrated patella drill guide 12 includes cutouts 51, 51' defining windows through which the surgeon may see the edge of the patella when the drill guide 12 is mounted on the patella.

The first end portion 45 and the second end portion 47 are substantially the same, differing only in size. Accordingly, only the details of first end portion 45 are described. It should be understood that the detailed description of the first end portion 45 applies to the second end portion 47 as well unless expressly distinguished. In the drawings, parts of the second end portion that are not separately described are identified with the same reference number as that used for the first end portion, followed by the prime symbol "'".

Figure 3:
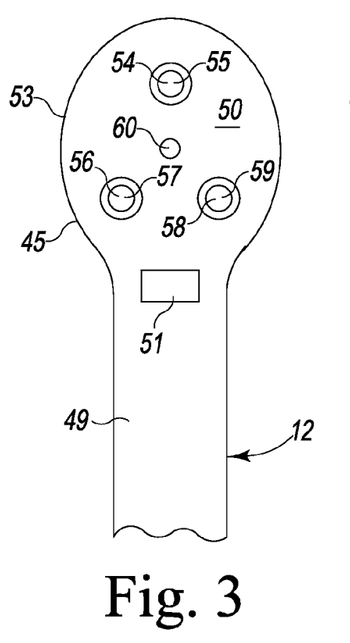
FIG. 3 is a top plan view of one end of patella drill guide of FIG. 2.
Figure 4:
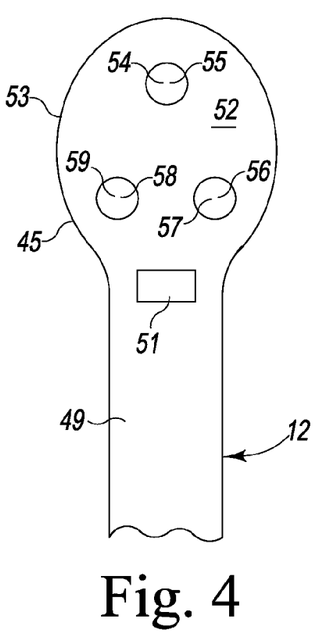
FIG. 4 is a bottom plan view of the end of the patella drill guide shown in FIGS. 2 and 3.
Figure 5:
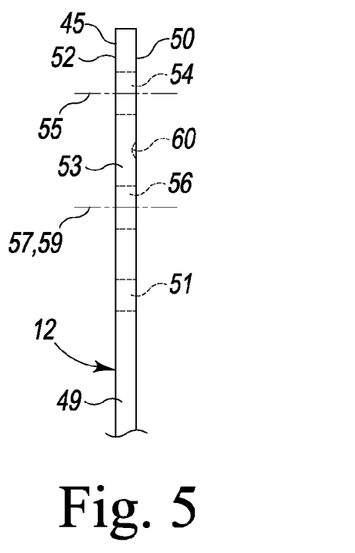
FIG. 5 is a side elevation of the end of the patella drill guide shown in FIGS. 2-4.
Figure 9:
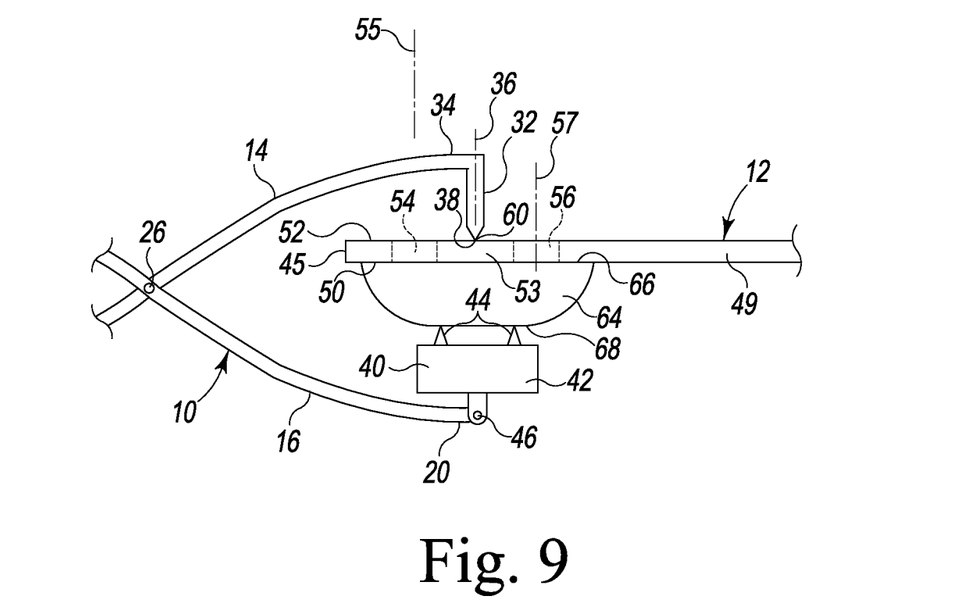
FIG. 9 is a side elevation view showing the clamp of FIG. 1 and one end of the patella drill guide of FIG. 2 clamped onto a patella, with the patella drill guide clamped to the resected posterior surface of the patella.

The first end portion 45 in the illustrated embodiment comprises a flat patella bone-facing surface 50 and an opposite upper surface 52 that is spaced from and parallel to the patella bone-facing surface 50. An edge 53 extends between and connects the bone-facing surface 50 and the upper surface 52. A plurality of drill guide bores 54, 56, 58 extend from the upper surface 52 to and through the patella bone-facing surface 50. As can be seen in FIGS. 2-4, the drill guide bores 54, 56, 58 in the illustrated embodiment are spaced in a triangular pattern on the end portion 47. As can be seen in FIGS. 2, 5 and 9, the drill guide bores have central longitudinal axes 55, 57, 59 that are perpendicular to the bone-facing surface 50 of the drill guide 12. Alternatively, the drill guide bores 54, 56, 58 may have a constant diameter and the top surface 52 of the drill guide may be used as a depth control stop.

The number of bores and spacing between the bores 54, 56, 58 correspond with the number and spacing of the mounting pegs on the patella implant component. The diameter of the bores 54, 56, 58 corresponds generally with the diameters of the mounting pegs on the patella implant component. It should be understood that the number, spacing and size of the bores may be adjusted from the illustrated embodiment, depending on the number, spacing and sizes of the mounting pegs on the patella implant component.

Each of the drill guide bores 54, 56, 58 may comprise two portions: a larger diameter portion extending down from the upper surface 52 and a smaller diameter portion extending from the larger diameter portion to and through the bone-facing surface 50 so that annular shoulders are defined at the junctions of the smaller and larger diameter portions. The diameters of the annular shoulders may correspond with the diameter of a collar portion of a depth-control drill bit (not shown). In use, the annular shoulders will limit movement of the drill bit into the patella by serving as a stop for the collar portion of the drill bit; the lengths of the smaller diameter portions of the drill guide bores 54, 56, 58 in this embodiment, together with the length of the fluted portion of the drill bit thereby control the depth of the holes drilled into the patella. The depth generally corresponds with the lengths of mounting pegs on the patella implant component.

The upper surface 52 of the first end portion 45 also includes a recess 60. In the illustrated embodiments, the recess 60 is spaced substantially equidistant from the drill guide bores 54, 56, 58 and has a substantially smaller diameter than the drill guide bores. The recess 60 may have a conical shape, and be sized and shaped to be complementary to the size and shape of the tip 38 of the first arm 14 of the clamp 10. Alternatively, the recess 60 may be sized and shaped to receive just the pointed end of the tip 38 of the first arm 14 of the clamp 10. In the first illustrated embodiment, the recess 60 is designed to receive the tip 38 so that the patella drill guide 12 may be clamped to the patella with the clamp 10 while being rotatable or pivotable with respect to the clamp 10 about an axis extending through the tip 38 and through the upper surface 52 and patella bone-facing surface 50 of the patella drill guide 12. Although it may be preferable to allow for relative rotation between the clamp 10 and the drill guide 12, it is also within the scope of the present invention to shape the tip 38 and the recess 60 to limit or prevent such relative rotation.

The recess 60 may comprise an indentation or dimple, as in the illustrated embodiment, wherein the recess extends from the upper surface 52 toward the patella bone-facing surface 50 but does not extend through the patella bone-facing surface. The recess may define a blind bore or, alternatively, may comprise a through-bore if desired. In the first illustrated embodiment, the recess 60 and the bores 54, 56, 58 have different depths.

FIG. 9 illustrates the clamp 10 and patella drill guide 12 of FIGS. 1-5 in use on a resected patella. In FIG. 9, the patella is shown at 64, the resected posterior surface of the patella at 66 and the native anterior surface of the patella at 68. When the first illustrated clamping patella drill guide 12 is mounted on a flat resected posterior surface 66, the flat patella bone-facing surface 50 of the patella drill guide is flat against the patella surface 66 and the upper surface 52 of the patella drill guide 12 is exposed. To hold the patella drill guide 12 in place, the surgeon would release the locking mechanism 28, 30 to open the space between the tip 38 of the first arm 14 and the bone-gripping member 40 of the second arm 16 so that the patella and patella drill guide 12 will fit between the tip 38 and the bone-gripping member 40. The surgeon would then place the point of the tip 38 in the recess 60 in the upper surface 52 of the drill guide 12 and then close the clamp 10, pivoting the arms 14, 16 and moving the spikes 44 of the bone-gripping member 40 into engagement with the anterior surface 68 of the patella 64. The bone-gripping member 40 may be pivoted about pivot connection 46 to optimize the orientation of the spikes 44 with respect to the patella anterior surface 68. If the clamp 10 has a locking mechanism, such as threaded rod 28 and wing nut 30, the locking mechanism can be engaged to thereby clamp the drill guide 12 to the patella 64.

In the first illustrated embodiment, the first arm 14 is shaped so that when the clamp 10 is locked in place to clamp the patella 64 and the patella drill guide 12 together, the central longitudinal axis 36 of the free end segment 32 of the first arm 14 is substantially perpendicular to the plane of the patella bone-facing surface 50 of the drill guide 12. It should be understood that although there are advantages to such a shape, the present invention is not limited to such a shape unless expressly called for in the claims.

With the patella drill guide 12 clamped to the patella 64 as shown, the patella drill guide 12 of the first illustrated embodiment is pivotable about an axis of rotation through the intersection of the point of the tip 38 and the recess 60, and through the bone-gripping member 40. This axis of rotation may be coincident with the central longitudinal axis 36 of the free end segment 32 of the first arm 14 and may be perpendicular to the patella bone-facing surface 50 of the drill guide 12.

Since the orientation of the bores 54, 56, 58 with respect to the posterior surface 66 of the patella 64 changes as the drill guide 12 is pivoted about the axis of rotation, and since the locations of the bores 54, 56, 58 correspond with the location of the mounting pegs on the implant component, the option of pivoting or rotating the base while it is clamped to the patella is advantageous, particularly for patella implant components that have anatomic or asymmetric articulation surface. The surgeon may adjust the orientation of the bores 54, 56, 58 intraoperatively and thereby optimize the orientation of the articulation surface of the patella implant component. Once the surgeon is satisfied with the orientation of the bores 54, 56, 58, the mounting holes for the pegs of the patella implant component may be drilled while the patella drill guide 12 remains clamped to the patella. Thus, the surgeon may drill these holes with one hand operating the drill and the other hand holding the end of the patella resection guide.

It should be noted that if the surgeon determines that a different size of patella implant component is required, the surgeon may turn the patella drilling guide 12 around and use the differently-sized second end portion 47 in the same manner as described above.

Variations of the above-described structure are available for achieving the advantages of the present invention. One variation is illustrated in an alternative embodiment of a patella drill guide in FIG. 6. In this embodiment, parts similar to those described above for the first embodiment are labeled with the same reference numbers as used in the above description and in FIGS. 2-5 and 9, followed by the letter "A" for the second embodiment. Another variation is illustrated in an alternative embodiment of a patella drill guide in FIGS. 11-12. In this embodiment, parts similar to those described above for the first embodiment are labeled with the same reference numbers as used in the above description and in FIGS. 2-6 and 9, followed by the letter "B" for the third embodiment. Unless a specific structure is described below, it should be assumed that the above description applies to like-numbered parts.

Figure 6:
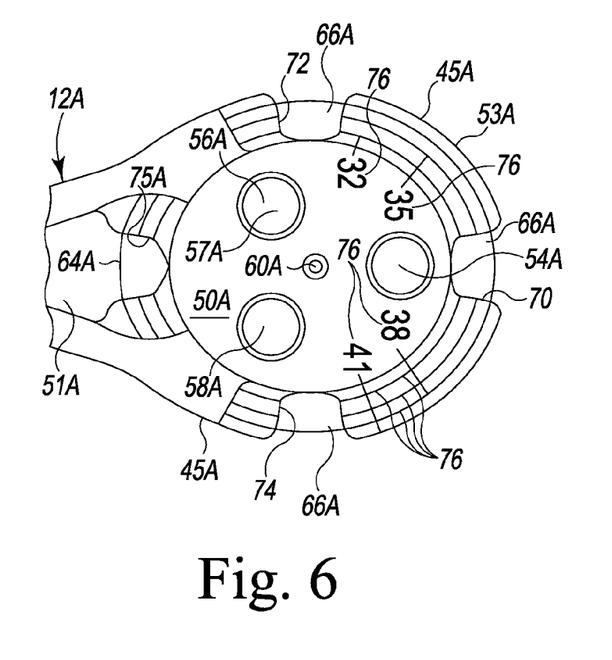
FIG. 6 is a top plan view of one end of an alternative embodiment of a patella drill guide that may be used in the patella drilling system of the present invention.

In the second illustrated embodiment shown in FIG. 6, the edge 53A, patella bone-facing surface 50A and upper surface 52A of the patella drill guide 12A have a plurality of spaced cut-outs or openings 70, 72, 74, 75 through which the resected posterior surface 66A of the patella 64A may be viewed. The upper surface 50A also includes sizing indicia 76 so that the surgeon can view the resected patella surface 66A juxtaposed with the sizing indicia 76 to determine the optimum size of patella implant component to be implanted. This embodiment is particularly beneficial if multiple sizes of patella implant components have commonly sized and positioned mounting pegs, so that the same drill guide 12A can be used for multiple sizes of patella implant components. If this embodiment is used, a single-ended patella drill guide may be used for multiple sizes of patella implant components, which may include all sizes of patella implant components in the implant system. The second illustrated patella drill guide 12A includes a recess 60A like the recess 60 of the first embodiment, and the second illustrated patella drill guide 12A may be used with the clamp 10 illustrated in FIGS. 1 and 9 in the manner described above.

Figure 11:
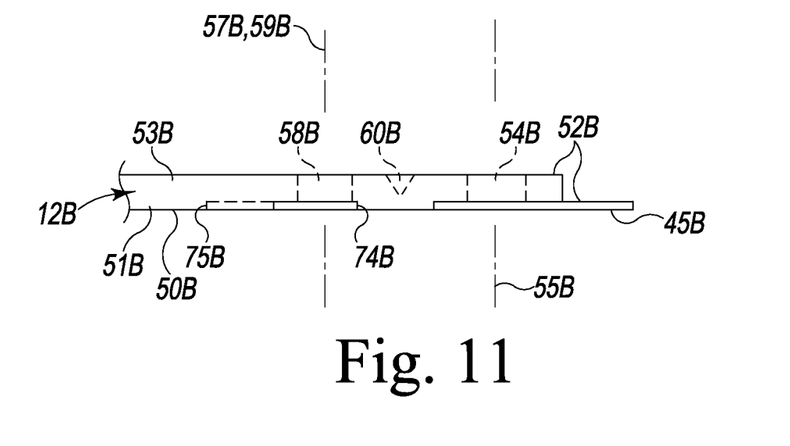
FIG. 11 is a side elevation of another alternative end of a patella drill guide, incorporating the features of the embodiment of FIG. 6 along with additional features.
Figure 12:
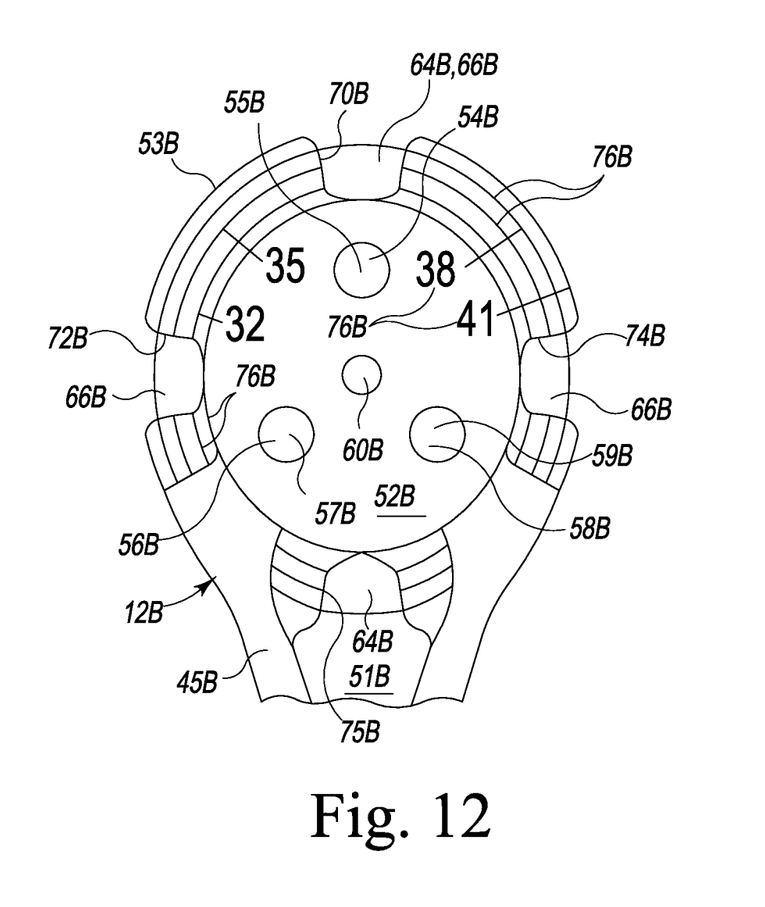
FIG. 12 is a top plan view of the end of the patella drill guide of FIG. 10.

The third embodiment shown in FIGS. 11-12 is similar to the embodiment of FIG. 6. In the embodiment of FIG. 6, the end portion 45A has a constant thickness between the top surface 25A and the patella bone-facing surface 24A. In the alternative embodiment of FIGS. 11-12, the thickness of the end portion 45B varies: near the cut-outs or recesses 70B, 72B, 74B, 75B. the thickness of the end portion 45B is less than the thickness near the drill guide bores 54B, 56B, 58B; for example, the thickness of the end portion 45B near the cut-outs or recesses 70B, 72B, 74B, 75B may be about 2 mm, while the thickness of the end portion 45B near the drill guide bores 54B, 56B, 58B may be about 6 mm. The varying thickness of the base portion may be advantageous in that the relatively thin areas around the cut-outs or recesses 70B, 72B, 74B, 75B make the sizing indicia 76B more proximate to the patella bone surface 66B and therefore more readable. In addition, the thicker center section around the drill guide bores 54B, 56B, 58B may be useful in reducing the number of drill bits included in the instrument set. Typically, an instrument set would include a drill bit with a depth stop for drilling holes at the appropriate depth to receive pegs of other components, such as the femoral implant component. The thicker center section of the end portion 45B would allow this same drill bit, with the same depth stop, to be used to drill the holes for the patella implant component at the appropriate depth for the patella implant component.

The clamp 10 and patella drill guides 12, 12A, 12B of the illustrated embodiments may be made of standard polymeric or metallic materials used in the field of surgical instruments, and may comprise assemblies of different such materials. Conventional manufacturing processes may be used to make the components. The invention is not limited to any particular material or manufacturing process unless expressly called for in the claims.

Figure 7:
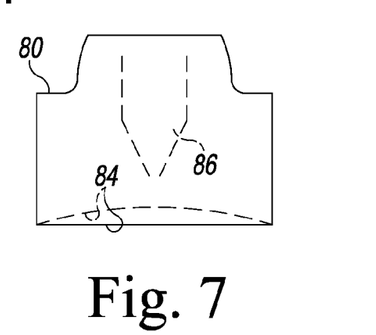
FIG. 7 is a side elevation of an illustrative cap that may optionally be included in the patella drilling system of the present invention.
Figure 8:
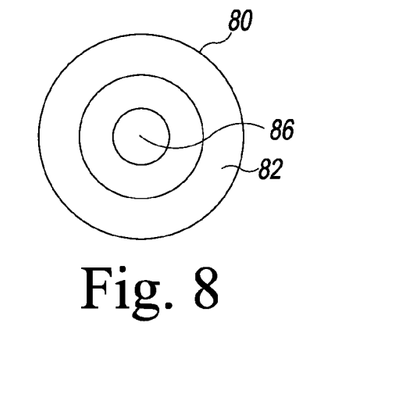
FIG. 8 is a top plan view of the cap of FIG. 7.
Figure 10:
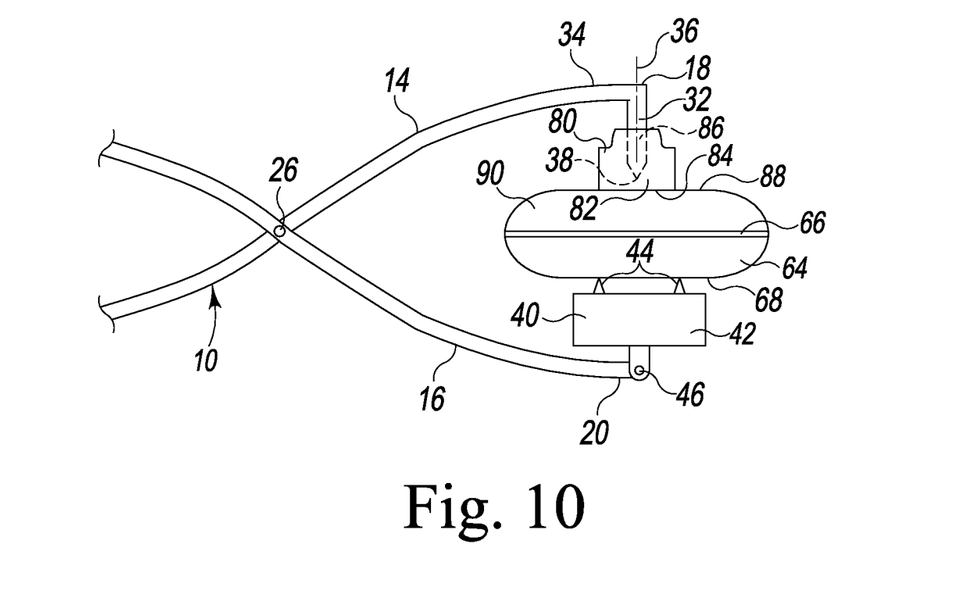
FIG. 10 is a side elevation view showing the clamp of FIG. 1 and the cap of FIGS. 7-8 clamped onto a patella, shown with a patellar implant component clamped by the cap, the bone-gripping member and the clamp to the prepared patella.

The patella drilling system may also include an optional element that may be used with the clamp 10 described above. This optional element is illustrated in FIGS. 7-8 and 10 and comprises a cap having a body 82. The body 82 has an end surface 84 and an aperture 86 overlying the end surface 84. The aperture 86 is sized and shaped so that the cap 80 may be selectively mounted on the free end segment 32 of the first arm 14 of the clamp.

The surface area of the end surface 84 of the cap 80 is substantially greater than the surface area of the tip 38 of the free end segment 32 of the first arm 14 of the clamp 10. The end surface 84 of the cap 80 is sized and shaped to be placed against the articulating surface 88 of the patella implant component 90, shown in FIG. 10. The end surface 84 is preferably shaped to complement the contour of the articulating surface 88 of the patella implant component 90. Thus, if the articulating surface 88 has a convex shape, the end surface 84 may have a corresponding concave shape.

The cap 80 may be useful in helping to properly cement the patella implant component 90 on the prepared posterior surface 66 of the patella 64. To hold the patella implant component 90 in place while the bone cement sets, the surgeon would release the locking mechanism to open the space between the tip 38 of the first arm 14 and the bone-gripping member 40 of the second arm so that the patella 64 and patella implant component 90 will fit between the tip 38 and the bone-gripping member 40. The surgeon would then place the point of the tip 38 in the aperture 86 in the cap 80 and then close the clamp 10 to pivot the arms 14, 16 to move the spikes 44 of the bone-gripping member 40 into engagement with the anterior surface 68 of the patella 64 and the end surface 84 of the cap 80 into engagement with the articulating surface 88 of the patella implant component 90. The bone-gripping member 40 may be pivoted about pivot connection 46 to optimize the orientation of the'spikes 44 with respect to the patella anterior surface 68. If the clamp 10 has a locking mechanism, the locking mechanism can be engaged to thereby clamp the implant component 90 to the patella 64 and hold the two together until the cement sets.

It will be appreciated that since the end surface 84 of the cap 80 is used to apply pressure to the articulating surface 88 of the patella implant component 90, it is desirable that at least the end surface 84 of the cap 80 be made of a material that will not damage the articulating surface 88. It is anticipated that a polymeric material will be used at least for the end surface 84 of the cap 80.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. Other features may be incorporated into the present invention, such as the features disclosed in U.S. Provisional Patent Application Ser. No. 61/540,040 entitled "Rotatable Patella Drill Guide", filed by Richard Spencer Jones, Martin W. Roche and Abraham P. Wright and in U.S. Provisional Patent Application Ser. No. 61/540,049 entitled "Clamping Patella Drill Guide", filed by Richard Spencer Jones, Martin W. Roche and Abraham P. Wright. The complete disclosure of these patent applications are incorporated by reference herein.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A patella drilling system for use in preparing a resected patellar bone surface to receive a prosthetic patellar implant component, the patella drilling system comprising:
    a patella drill guide comprising a flat patella bone-facing surface, an opposite upper surface and an edge extending between the flat patella bone-facing surface and the opposite upper surface, the edge including a plurality of spaced openings;
    a plurality of spaced drill guide bores extending from the upper surface to and through the flat patella bone-facing surface, each drill guide bore having a central longitudinal axis that is perpendicular to the flat patella bone-facing surface;
    a recess in the upper surface of the patella drill guide;
    a clamp comprising a first arm and a second arm, the first arm having a first end and a second end and the second arm having a first end and a second end;
    the first end of the first arm having a free end segment adjacent to a contiguous segment and including a tip that is sized and shaped to be received in the recess in the upper surface of the patella drill guide;
    the first end of the second arm including a bone-gripping member, the bone gripping member including a spike;
    wherein:
    the first arm and second arm are connected through a pivotal connection and are pivotable with respect to each other to a position wherein the end segment of the first arm is oriented substantially perpendicular to the patella bone-facing surface of the drill guide, the tip of the first arm is received within the recess of the patella drill guide and the bone-gripping member extends toward the bone-facing surface of the patella drill guide;
    the patella drill guide has a thickness between the upper surface and the flat patella bone-facing surface; and
    the thickness of the patella drill guide adjacent to the drill guide bores is greater than the thickness of the patella drill guide adjacent to the spaced openings;
    the drill guide bores are spaced from the spaced openings; and
    the upper surface of the drill guide includes sizing indicia adjacent to the spaced openings, the sizing indicia including a plurality of lines intersecting the spaced openings.

2. The patella drilling system of claim 1 wherein the bone-gripping member and the second arm comprise discrete components connected through a pivotal connection.

3. The patella drilling system of claim 1 wherein when the patella drill guide is mounted on a patella, with the bone-gripping member engaging one surface of the patella, with the patella drill guide bone-facing surface engaging another surface of the patella and with the tip received in the recess, the patella drill guide is pivotable with respect to the clamp about an axis of rotation through the tip and through the bone-gripping member, the axis being substantially perpendicular to the patella bone-facing surface.

4. The patella drilling system of claim 1 wherein the bone-gripping member comprises a base and a plurality of spikes extending out from the base.

5. The patella drilling system of claim 4 wherein the base of the bone-gripping member is connected to the first end of the second arm through a pivotal connection.

6. The patella drilling system of claim 1 wherein the recess and the drill guide bore have different diameters.

7. The patella drilling system of claim 6 wherein the recess and the drill guide bore have different depths.

8. The patella drilling system of claim 1 wherein the recess extends from the upper surface of the drill guide bore but does not extend through the patella bone-facing surface of the patella drill guide.

9. The patella drilling system of claim 1 further comprising a cap including a body having an end surface and an aperture overlying the end surface, wherein the aperture is sized and shaped to be complementary to at least a portion of the free end segment of the first arm so that the cap may be selectively mounted on the free end segment of the first arm.

10. The patella drilling system of claim 9 wherein the end surface of the cap has a surface area greater than the surface area of the tip of the first arm of the clamp.

11. The patella drilling system of claim 1 wherein the spaced openings are sized and shaped so that portions of the resected surface of the patella are visible through the spaced openings.

12. The patella drilling system of claim 1 wherein the recess is spaced from the spaced drill guide bores and the spaced openings.

13. The patella drilling system of claim 12 wherein the recess is equidistant from each drill guide bore.

* * * * *